(12) United States Patent
Kim et al.

(10) Patent No.: US 11,052,334 B2
(45) Date of Patent: Jul. 6, 2021

(54) ULTRAVIOLET MODULE AND LIQUID DISPENSER INCLUDING SAME (71) Applicant: LG ELECTRONICS INC., Seoul (KR)

(72) Inventors: Youngjin Kim, Seoul (KR); Myounggon Kim, Seoul (KR); Kowoon Baek, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 16/469,549

(22) PCT Filed: Dec. 18, 2017

(86) PCT No.: PCT/KR2017/014973
§ 371 (c)(1),
(2) Date: Jun. 13, 2019

(87) PCT Pub. No.: WO2018/111058
PCT Pub. Date: Jun. 21, 2018

(65) Prior Publication Data
US 2020/0114290 A1    Apr. 16, 2020

(30) Foreign Application Priority Data

Dec. 16, 2016    (KR) .................... 10-2016-0172959

(51) Int. Cl.
*B01D 35/16* (2006.01)
*A61L 2/10* (2006.01)
(Continued)

(52) U.S. Cl.
CPC ............. *B01D 35/16* (2013.01); *A61L 2/10* (2013.01); *A61L 2/26* (2013.01); *B01D 35/04* (2013.01);
(Continued)

(58) Field of Classification Search
USPC ........................................... 250/438
See application file for complete search history.

(56) References Cited

U.S. PATENT DOCUMENTS 5,536,395 A * 7/1996 Kuennen ................. C02F 1/283
                                                               210/87
7,002,161 B2 * 2/2006 Greene .................... C02F 1/008
                                                               210/94
(Continued)

FOREIGN PATENT DOCUMENTS

KR    20-0338582    1/2004
KR    20-0393066    8/2005
(Continued)

OTHER PUBLICATIONS

International Search Report (with English Translation) and Written Opinion dated Apr. 16, 2018 issued in Application No. PCT/KR2017/014973.

*Primary Examiner* — Phillip A Johnston
(74) *Attorney, Agent, or Firm* — Ked & Associates. LLP (57) ABSTRACT

A water purifier according to an embodiment of the present invention may include a housing accommodating components for generating cold water and/or hot water; a water cock which protrudes from a front surface of the housing, the water cock being configured to discharge the cold water or the hot water; a control panel which is provided so as to input a command for discharging the cold water or the hot water; a sterilization module which is detachably mounted on the water cock, the sterilization module being configured to emit ultraviolet rays for sterilizing the inside of the water cock; and a fastening part which is formed on the water cock and the sterilization module, respectively, so that the sterilization module can be attached to and detached from the water cock.

6 Claims, 6 Drawing Sheets

(51) Int. Cl.
   *A61L 2/26*     (2006.01)
   *B01D 35/04*    (2006.01)
   *B67D 1/12*     (2006.01)
   *C02F 1/00*     (2006.01)

(52) U.S. Cl.
   CPC ............ *B67D 1/1202* (2013.01); *C02F 1/003* (2013.01); *A61L 2202/11* (2013.01); *A61L 2202/122* (2013.01); *C02F 2303/04* (2013.01)

(56) References Cited

U.S. PATENT DOCUMENTS

| | | | |
|---|---|---|---|
| 8,128,820 B2* | 3/2012 | Wu ................... | C02F 1/003 210/251 |
| 9,346,687 B1* | 5/2016 | Matthews ........... | C02F 1/325 |
| 2013/0234037 A1* | 9/2013 | Moglan ............... | C02F 1/325 250/432 R |
| 2014/0158905 A1* | 6/2014 | Hoang ................ | C02F 1/325 250/435 |
| 2017/0022073 A1* | 1/2017 | Penhale .............. | H01J 61/02 |

FOREIGN PATENT DOCUMENTS

| | | |
|---|---|---|
| KR | 10-2010-0131802 | 12/2010 |
| KR | 10-1094257 | 12/2011 |
| KR | 10-2012-0012710 | 2/2012 |
| KR | 10-1621873 | 5/2016 |

* cited by examiner

ULTRAVIOLET MODULE AND LIQUID
DISPENSER INCLUDING SAME

CROSS-REFERENCE TO RELATED PATENT
APPLICATIONS

This application is a U.S. National Stage Application under 35 U.S.C. § 371 of PCT Application No. PCT/KR2017/014973, filed Dec. 18, 2017, which claims priority to Korean Patent Application No. 10-2016-0172959, filed Dec. 16, 2016, whose entire disclosures are hereby incorporated by reference.

TECHNICAL FIELD

The present invention relates to a sterilization module and a water purifier including the same.

BACKGROUND ART

A water purifier can be defined as a device which filters harmful elements such as foreign substances or heavy metals contained in tap water.

A water purifying filter is used to purify the tap water flowing into the water purifier, and an ultraviolet sterilization method is used to sterilize the inside of a water cock from which water is discharged.

Korean Utility Model Registration No. 20-0393066 (Aug. 9, 2005) which is the related art discloses a structure for sterilizing water inside a water cock by mounting an LED which emits ultraviolet rays on an upper side of a water cock.

DISCLOSURE

Technical Problem

In a case of the related art, there are following problems.

Specifically, a part of light irradiated downward from the ultraviolet ray emitting LED mounted on an upper surface of the water cock may be exposed to the outside of the water purifier through the water cock, and the user may be injured by the exposed ultraviolet rays.

Therefore, there is a disadvantage in that there is a limit in increasing the power of the light emitting unit.

The present invention is proposed to solve the above problems.

Technical Solution

In order to achieve the above objective, according to an embodiment of the present invention, there is provided a water purifier which may include a housing accommodating components for generating cold water and/or hot water; a water cock which protrudes from a front surface of the housing, the water cock being configured to discharge the cold water or the hot water; a control panel which is provided so as to input a command for discharging the cold water or the hot water; a sterilization module which is detachably mounted on the water cock, the sterilization module being configured to emit ultraviolet rays for sterilizing the inside of the water cock; and a fastening part which is formed on the water cock and the sterilization module, respectively, so that the sterilization module can be attached to and detached from the water cock.

In order to achieve the above objective, according to an embodiment of the present invention, there is provided a sterilization module which may include a module case which has a recessed part allowing a water outflow pipe of a water purifier discharging potable water to be inserted therein; a light emitting unit which is mounted on a bottom part of the recessed part to emit ultraviolet rays; a pair of terminal parts which are formed on an upper surface of the module case and is in contact with the terminal parts provided on a side of the water purifier when the module case is coupled to the water outflow pipe; and a power line which is embedded in the module case and connects the light emitting unit and the pair of terminal parts.

Advantageous Effect

The sterilization module according to the embodiment of the present invention having the configurations described above and the water purifier having the same have the following effects.

First, since the sterilization module according to the embodiment of the present invention can be detachably attached to the water cock of the water purifier, it is not necessary to incorporate a sterilization module including an ultraviolet ray emitting unit inside the water cock. Therefore, there is an advantage that a change in the internal structure of the water cock of the water purifier is not required much.

Second, there is an advantage that it is not necessary to change the shape of the water outflow passage to prevent the ultraviolet rays from leaking out of the water cock.

Third, when the sterilization module according to the embodiment of the present invention is mounted on the water cock, since the ultraviolet rays do not leak to the outside, there is an advantage that the power can be higher than that of the built-in sterilization module, and as a result, the sterilizing mode time can be shortened.

Fourth, in a state where the sterilization module is separated from the water cock of the water purifier, since power is not supplied to the light emitting unit, there is no fear that the ultraviolet rays are exposed to the outside and the user is injured, and thus there is an advantage that stability of use is ensured.

Fifth, since the sterilization module can be separated from the water cock of the water purifier, the sterilization module can be easily cleaned.

BEST MODE

Hereinafter, a water purifier including a water cock sterilization module according to an embodiment of the present invention will be described in detail with reference to the drawings.

Figure 1:
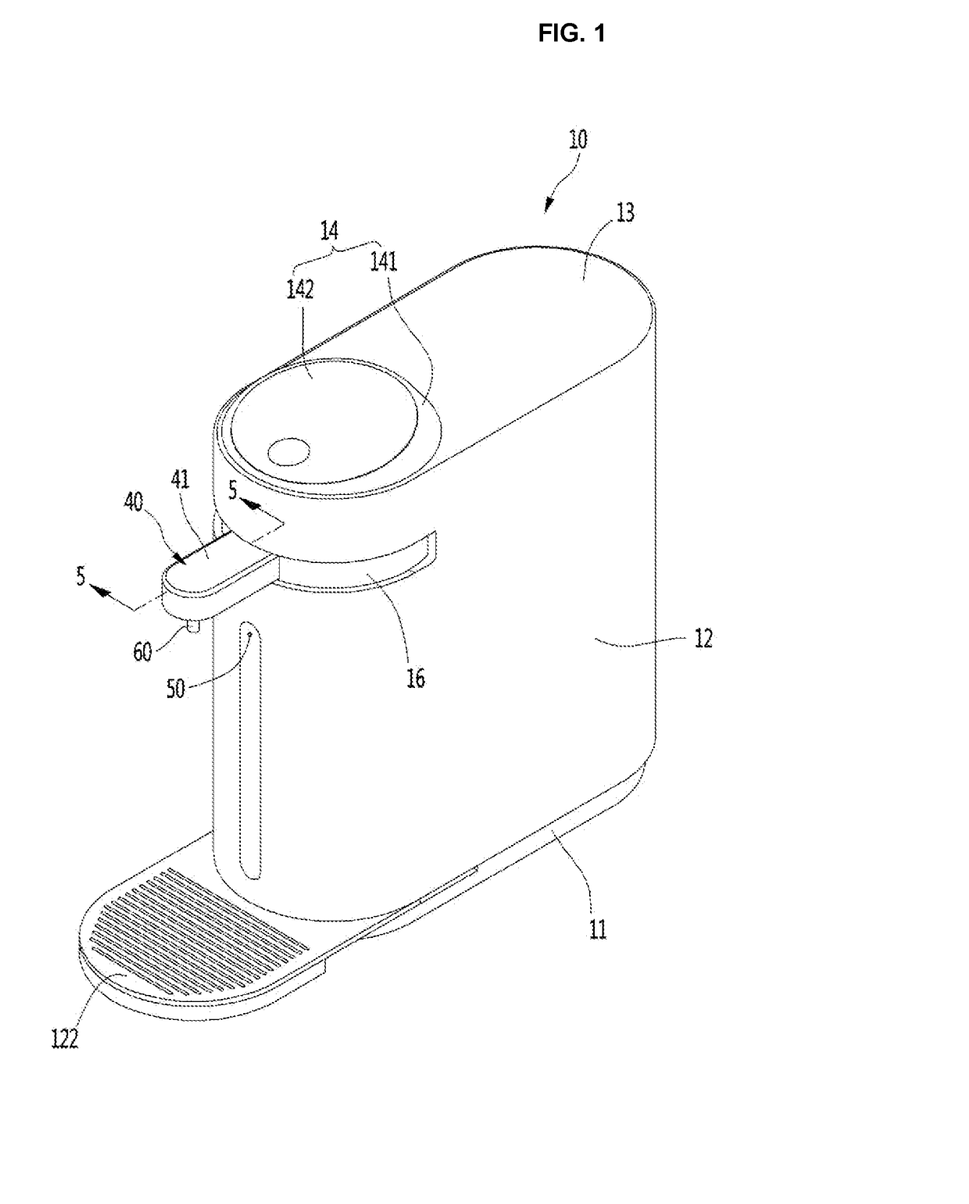
FIG. 1 is a perspective view illustrating a water purifier equipped with a water cock sterilization mechanism according to an embodiment of the present invention.

FIG. 1 is a perspective view illustrating a water purifier equipped with a water cock sterilization mechanism according to an embodiment of the present invention.

Referring to FIG. 1, the water purifier 10 according to the embodiment of the present invention may include a direct watering type cooling and heating water purifier for cooling or heating water directly supplied from an external water supply source and discharging the water, but is not limited thereto. In other words, the sterilization mechanism of the present invention can be also applied to a water purifier having a reservoir.

In detail, the water purifier 10 may include a base 11 constituting a bottom part, a housing 12 placed on an upper surface edge of the base 11, a cover 13 covering an opened upper surface of the housing 12, a control panel 14 formed on the upper surface of the cover 13, and a water cock 40 protruding from the outer circumferential surface of the housing 12.

More specifically, a part where the water cock 40 is formed may be defined as a front surface of the water purifier 10, and an opposite surface thereto may be defined as a rear surface of the water purifier 10.

In addition, the control panel 14 may be formed at a position close to the front end of the water purifier 10 and may be formed at a position close to the upper surface center part or the rear end of the water purifier 10 according to design conditions. In addition, the control panel 14 may be inclined in such a manner that the height of the control panel 14 increases toward the rear so that the control panel 14 can be easily recognized by the user's eyes positioned in front of the water cock 40.

In detail, the control panel 14 may include a panel main body 141 having a rear end protruding higher than the front end of the water purifier 10 from the upper surface thereof and a panel cover 142 covering the upper surface of the panel main body 141. In addition, the control panel 14 may include a plurality of operation buttons including a power button. For example, the operation buttons provided on the control panel 14 may include a power button, a water discharge button, a button for selecting the type of water to be discharged, a button for setting the water temperature, a button for setting the amount of water to be discharged, and the like.

In addition, the water cock 40 may be extended forward by a predetermined length from the front end of the water purifier 10 and may be rotatably mounted within a range of 90 degrees from the center of the front end of the water purifier 10 in a lateral direction, respectively. In other words, the water cock 40 can rotate 180 degrees in total. Of course, the water cock 40 may be fixed to the front surface of the housing 12.

In addition, a rotation guide 16 having a circular band shape may be mounted on the rear end of the water cock 40 so that the water cock 40 can rotate. The water cock 40 and the rotation guide 16 can be injection-molded into one body or can be formed as separate parts and joined as one body by a fastening member.

In addition, a guide hole 121 for guiding the rotation of the water cock 40 may be formed on the front surface of the housing 12 and the water cock 40 can rotate along the guide hole 121 by 90 degrees in the lateral direction.

In addition, a proximity sensor 50 for detecting the approach of the user is mounted on the front surface of the housing 12 so that in a case where the user approaches the water purifier 10 during sterilization, the proximity sensor can detect the approach of the user and thus can transmit the approach of the user to a control unit (not illustrated) of the water purifier. The control unit may be provided inside the control panel 14.

In addition, a tray 122 is mounted on the lower end of the front surface of the housing 12 so that a part of the water discharged from the water cock 40 or a water drop falling from the water cock 40 can be collected. The tray 122 may also be designed so as to be rotatable by a predetermined angle designed in the same manner as in the water cock 40 in the lateral direction.

In addition, the water cock 40 may include a water inflow part 41 (or a water inflow pipe) extending forward from the front surface of the housing 12 and a water outflow part 42 (or a water outflow pipe) (see FIG. 2) extending downward from an end of the water inflow part 41.

In addition, a sterilization module 60 is mounted on the outer circumferential surface of the water outflow part 42 and the sterilization module 60 is detachable from the water outflow part 42 of the water cork 40.

Figure 2:
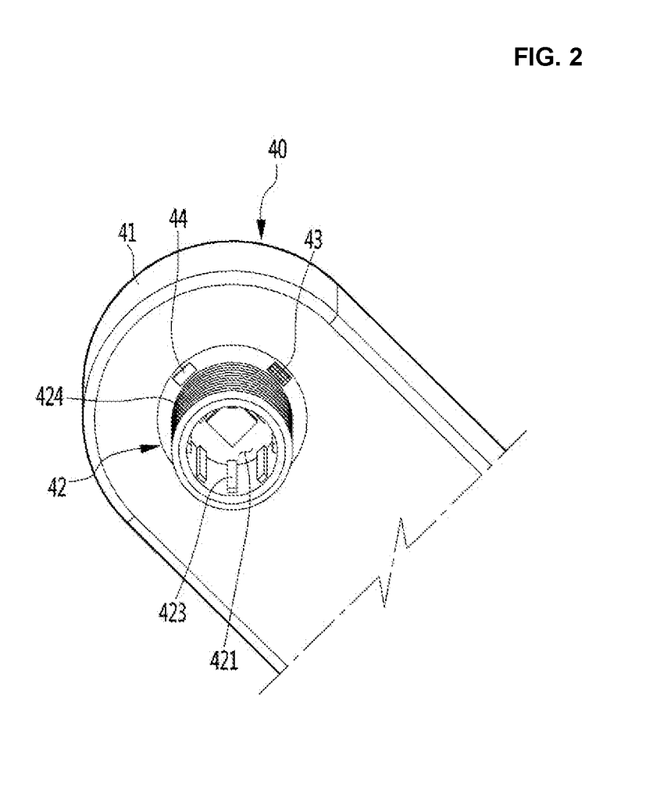
FIG. 2 is a bottom perspective view of a water cock constituting a water purifier according to an embodiment of the present invention.

FIG. 2 is a bottom perspective view of a water cock constituting a water purifier according to an embodiment of the present invention.

Referring to FIG. 2, the water outflow part 42 extends a predetermined length from the bottom end of the water inflow part 41 constituting the water cock 40.

One or a plurality of magnets 44 may be mounted on the bottom surface of the water inflow part 41 corresponding to the outside of the water outflow part 42. A pair of magnets 44 may be provided at positions facing each other or may have a circular band shape surrounding the outer edge of the water outflow part 42. The magnet 44 may be provided as a fastening means for fixing the sterilization module 60 to the bottom surface of the water inflow part 41.

Alternatively, a screw thread 424 may be formed on the outer circumferential surface of the water outflow part 42 so that the sterilization module 61 may be screwed to the outer circumferential surface of the water outflow part 42. Here, only one of the magnet 44 and the screw thread 424 may be provided for coupling the sterilization module 60. In addition to the magnet or threaded structure, other types of fastening means are also applicable such that the sterilization module 60 is detachably coupled to the outer circumferential surface of the water outflow part 42.

Meanwhile, a water outflow passage 421 is formed inside the water outflow part 42, and the water outflow passage 421 is formed in a cylindrical shape having a constant diameter, or a truncated cone shape in which the cross-sectional diameter progressively decreases toward the lower end.

In addition, a plurality of ribs 423 may be formed on the inner circumferential surface of the water outflow part 42 so that potable water flowing through the water inflow part 41 can flow down directly while passing over the water outlet passage 421 without splashing to the side. The plurality of ribs 423 may be spaced apart from each other by a predetermined distance in the circumferential direction of the water outflow part 42.

In addition, a terminal part 43 may be formed on the bottom surface of the water inflow part 41 corresponding to the outside of the water outlet part 42.

Figure 3:
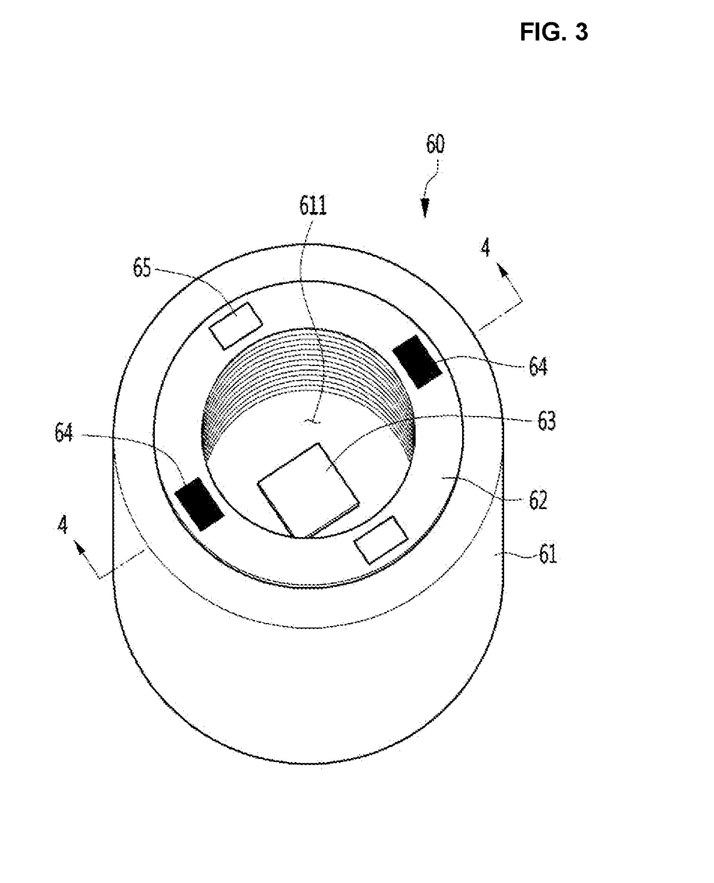
FIG. 3 is a perspective view of a sterilization module used for water cock sterilization of a water purifier according to the first embodiment of the present invention.
Figure 4:
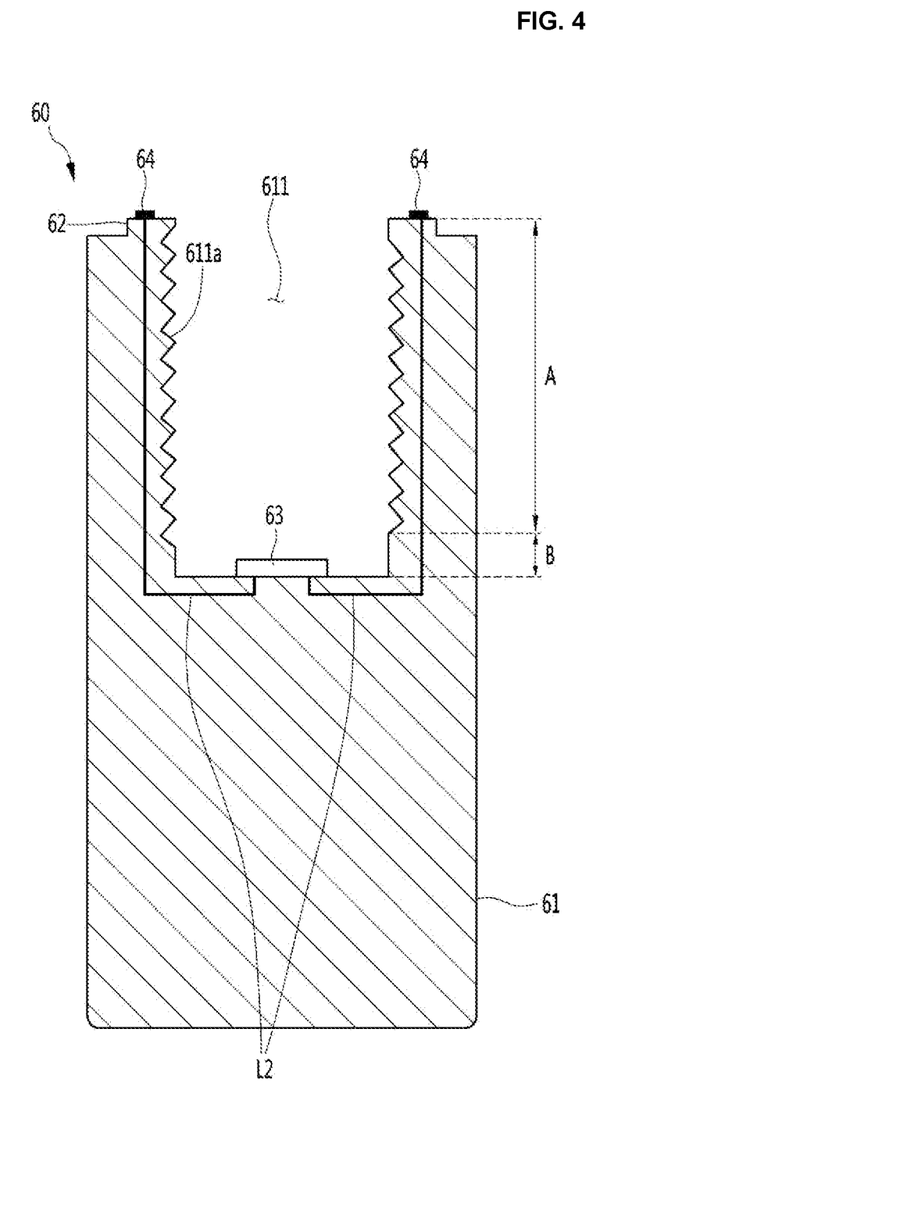
FIG. 4 is a longitudinal sectional view of a sterilization module taken along line 4-4 of FIG. 3.

FIG. 3 is a perspective view of a sterilization module used for water cock sterilization of a water purifier according to the first embodiment of the present invention, and FIG. 4 is a longitudinal sectional view of a sterilization module taken along line 4-4 of FIG. 3.

Referring to FIGS. 3 and 4, a sterilization module 60 according to an embodiment of the present invention may include a module case 61 having a cylindrical or polygonal shape and having a recessed part 611 formed therein, a light emitting unit 63 mounted on a bottom part of the recessed part 611, and a terminal part 64 formed on the upper surface of the module case 611.

In detail, the light emitting unit 63 may include a light emitting element including an LED element emitting ultraviolet rays having a wavelength of 380 nm, and a substrate on which the light emitting element is mounted. The light emitting unit 63 is disposed at the center of the bottom part of the recessed part 611 so that ultraviolet rays emitted in a lambertian form from the light emitting element are irradiated to the inside of the water outflow part 42.

A power supply line L2 for connecting the terminal unit 64 and the light emitting unit 63 may be embedded in the module case 61. The power supply line L2 may include a (+) power supply line and a negative (−) power supply line, and the two power supply lines may be connected to the pair of terminal units 64, respectively.

In addition, a sleeve 62 may protrude from the upper surface of the module case 61 corresponding to the edge of the recessed part 611 at a predetermined height. The terminal part 64 may be provided on the upper surface of the sleeve 62.

In addition, in a case where the magnet 44 is used, as a means for mounting the sterilization module 60 on the water cock 40, the magnet 44 may be provided on the upper surface of the sleeve 62. However, the sleeve 62 does not necessarily have to protrude from the upper surface of the module case 61.

In a case where a screw thread coupling method is applied as a means for mounting the sterilization module 50 on the water cork 40, a screw thread 611a may be formed on the inner circumferential surface of the recessed part 611. A screw thread 424 formed on an outer circumferential surface of the water outflow part 42 may be coupled to the screw thread 611a.

The recessed part 611 is space into which the water outflow part 42 constituting the water cock 40 is inserted and the depth of the recessed part 611 may be longer than the length of the water outflow part 42.

Figure 5:
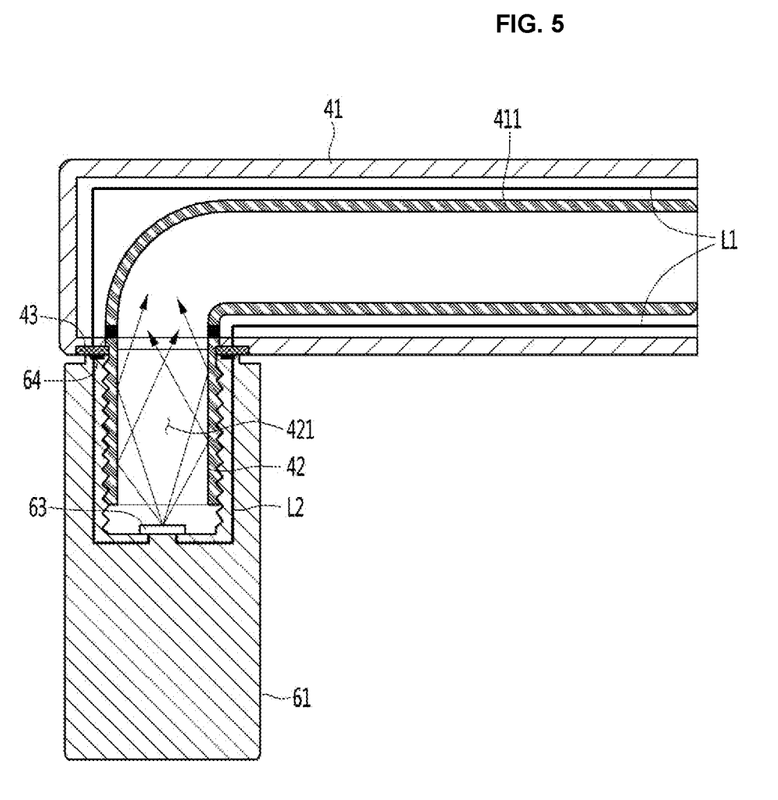
FIG. 5 is a longitudinal sectional view taken along line 5-5 in FIG. 1, and is a sectional view illustrating a state where the sterilization module according to the first embodiment is mounted.

FIG. 5 is a longitudinal sectional view taken along line 5-5 in FIG. 1, and is a sectional view illustrating a state where the sterilization module according to the first embodiment is mounted.

Referring to FIG. 5, the water outflow part 42 is inserted into a recessed part 611 of the sterilization module 60.

In addition, as a method for coupling the sterilization module 60 to the water outflow part 42. First, a method in which no screw thread is formed on the inner circumferential surface of the recessed part 611 and the outer circumferential surface of the water outflow part 42, a magnet 65 mounted on the upper surface of the sleeve 62 may be closely contacted with the magnet 44 mounted on the bottom surface of the water inflow part 41 by the magnetic force can be used. In other words, the water outflow part 42 is smoothly fitted into the recessed part 611 of the module case 61 so that the sterilization module 60 can be fixed to the bottom surface of the water inflow part 41 by the attractive force of the magnets.

Second, the magnets are not provided, and a screw thread 611a is formed on the inner circumferential surface of the recessed part 611 and a screw thread is formed on the outer circumferential surface of the water outflow part 42, and thus the screw threads can be screwed together.

In addition to the coupling methods presented above, although other coupling structures may be applied, commonly, when the sterilization module 60 is mounted on the bottom surface of the water inflow part 41, the terminal parts 43 and 64 have to be brought into contact with each other.

For example, in a case of a coupling structure using a magnet, as illustrated in the drawings, a pair of magnets are disposed at positions facing each other, and the pair of terminal parts 43 are disposed on a line orthogonal to a line connecting the pair of magnets, and thus the magnet of the water inflow part 41 can be attached to the magnet 65 of the sterilization module 60 and the terminal parts 43 and 64 can be also accurately brought into contact with each other.

In addition, in a case where the screw coupling structure is applied, when the sterilization module 60 is rotated and fitted into the water outflow part 42 and thus the sterilization module 60 is rotated until the sterilization module 60 is not rotated any further, the terminal parts 43 and 64 can be brought into contact with each other.

Meanwhile, a power supply line L1 extending from the terminal parts 43 is embedded in the water inflow part 41 and the power supply line L1 may be connected to the control panel 14. The power line L1 also includes a (+) power source line and a (−) power source line. When the sterilization module 60 is coupled to the water outflow part 42, the power supplied to the water purifier 10 is supplied to the light emitting unit 63 by the contact of the terminal parts 43 and 64.

The ultraviolet rays emitted from the light emitting unit 63 is reflected by being collided with the inner circumferential surface of the water outflow passage 421 to sterilize the inner circumferential surface of the water outflow passage 421 and the potable water remaining in the water outflow passage 421.

Figure 6:
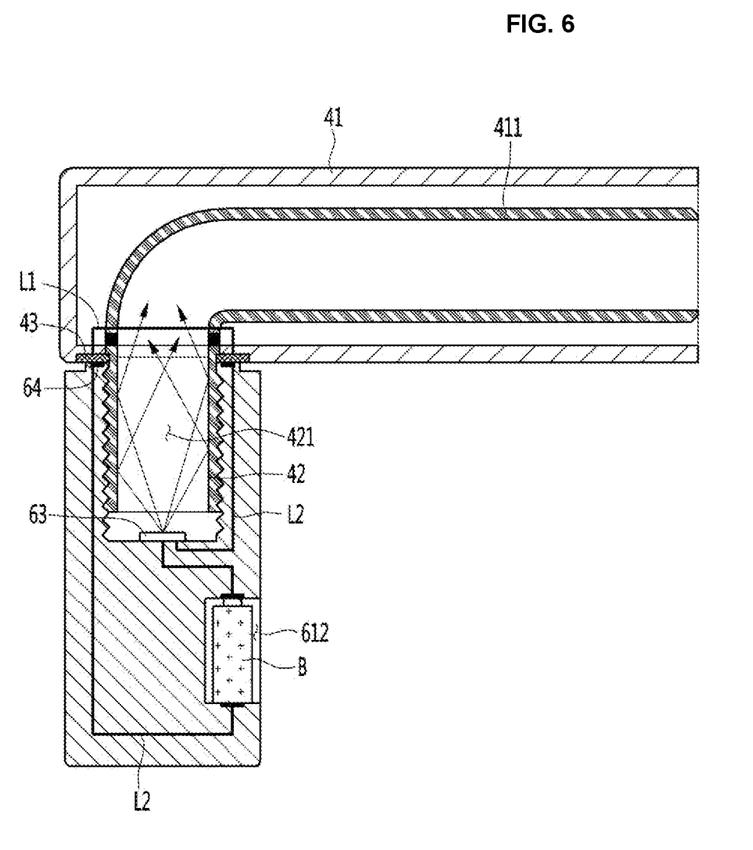
FIG. 6 is a longitudinal sectional view taken along line 5-5 of FIG. 1, and is a sectional view illustrating a state where the sterilization module according to the second embodiment is mounted.

FIG. 6 is a longitudinal sectional view taken along line 5-5 of FIG. 1 and is a sectional view illustrating a state where the sterilization module according to the second embodiment is mounted.

Referring to FIG. 6, the sterilization module 60 according to the second embodiment of the present invention is characterized in that a battery is mounted therein.

In detail, the sterilization module 60 according to the present embodiment is substantially the same as the structure of the sterilization module according to the first embodiment, in which there is a difference in that a battery mounting part 612 for mounting a battery is recessed inside the module case 61.

More specifically, the terminal part may be formed on the inner circumferential surface of the battery mounting part 612, particularly, on the inner circumferential surface of the battery where the positive electrode and the negative electrode are in contact with each other. As illustrated in the drawings, any one of the power supply lines L1 embedded in the case module 61 is disconnected and thus connected to the positive electrode terminal part and the negative electrode terminal part formed in the battery mounting part 612, respectively.

In addition, the power supply line L1 embedded in the water inflow part 41 does not extend toward the control panel 14 but connects the pair of terminal parts 43.

With this circuit configuration, when the battery B is mounted on the battery mounting part 612 and the sterilization module 60 is coupled to the bottom surface of the water inflow part 41, current charged into the battery B flows along the power supply lines L1 and L2. Then, a current flows to the light emitting unit 63, and ultraviolet rays are irradiated from the light emitting unit 63.

Meanwhile, The depth of the recessed part 611 is formed to be longer than the length of the water outflow part 42m and thus in a case where the sterilization module 60 is mounted on the outer circumferential surface of the water outflow part 42, it is preferable that the lower end of the water outflow part 42 is spaced apart from the bottom of the recessed part 611 by a predetermined distance B. In other words, the depth of the recessed part 611 may be defined as the sum of the length A of the coupling part and the separation distance B of the water outflow part 42.

Because the light emitting element constituting the light emitting unit 63 is an LED element which emits ultraviolet rays in the lam bertian form, this is emitted while being spread with a predetermined directivity angle. Therefore, in a case where the lower end of the water outflow part 42 touches the lower end of the recessed part 611, ultraviolet rays emitted from the light emitting unit 63 do not reach the lower end of the water outflow part 42, and thus the lower end of the water outflow part 42 may not be sterilized.

In order to prevent such a phenomenon, it is preferable that a separation space is formed between the lower end of the water outflow part 42 and the bottom of the recessed part 611. This is also applied equally to the sterilization module 60 according to the first embodiment.

The invention claimed is:

1. A liquid dispenser comprising:
   a housing accommodating components for generating a cold liquid and/or a hot liquid;
   a cock which protrudes from the housing, the cock being configured to discharge a liquid and including:
      an inflow pipe laterally extending from a side of the housing; and
      an outflow pipe extending downward from a bottom of the inflow pipe;
   a control panel which is provided so as to input a command for discharging the liquid;
   a sterilization module which is detachably mounted on the outflow pipe of the cock to sterilize the cock; and
   a fastener which is formed on at least one of the cock or the sterilization module so that the sterilization module can be selectively attached to or detached from the outflow pipe of the cock for sterilization,
   wherein the cock further includes first terminals formed on a bottom surface of the inflow pipe corresponding to an outside of the outflow pipe,
   wherein the sterilization module includes:
      a module case in which a recess to receive a whole of the outflow pipe is formed;
      a light emitting unit mounted on a bottom of the recess to emit ultraviolet rays upwardly towards an inside of the outflow pipe; and
      second terminals which are formed on an upper surface of the module case, and
   wherein the recess is recessed from an upper end of the module case to a depth longer than the outflow pipe, such that a lower end of the outflow pipe is spaced apart from the bottom of the recess.

2. The liquid dispenser of claim 1, further comprising:
   first power lines which are provided at the inflow pipe and electrically connect first terminals and a control panel of the liquid dispenser; and
   a power supply line which is embedded in the module case and electrically connects second terminals and the light emitting element,
   wherein when the sterilization module is mounted on the outer circumferential surface of the outflow pipe, the first terminals and the second terminals are in contact with each other, and power is supplied to the light emitting element.

3. The liquid dispenser of claim 1, further comprising:
   a first power line which is provided inside the inflow pipe and connects the first terminals when the sterilization module is mounted on the cock;
   a battery mount which is recessed in the module case;
   battery terminals which are formed on the battery mount; and
   a second power line which is embedded in the module case and electrically connects the second terminals, the battery terminals, and the light emitting element to each other.

4. The liquid dispenser of claim 3, further comprising:
   a battery which is configured to be received on the battery mount,
   wherein, when the sterilization module is mounted on the outer circumferential surface of the outflow pipe, the first terminals and the second terminals are in contact with each other such that power from the battery is supplied to the light emitting element.

5. The liquid dispenser of claim 1,
   wherein the fastener includes:
      a first magnet which is provided on an upper surface of the module case; and
      a second magnet which is provided on a bottom surface of the inflow pipe and is configured to be coupled to the first magnet by a magnetic force when the sterilization module is mounted on the cock.

6. The liquid dispenser of claim 1,
   wherein the fastening fastener includes:
      a first screw thread which is formed on an inner circumferential surface of the recess; and
      a second screw thread which is formed on an outer circumferential surface of the outflow pipe and is configured to engage the first screw thread when the sterilization module is mounted on the cock.

* * * * *